United States Patent
Williams

(10) Patent No.: US 9,113,886 B2
(45) Date of Patent: *Aug. 25, 2015

(54) TILT TOP ANVIL WITH TORSION SPRING

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/524,416

(22) Filed: Oct. 27, 2014

(65) Prior Publication Data

US 2015/0041519 A1    Feb. 12, 2015

Related U.S. Application Data

(63) Continuation of application No. 14/207,729, filed on Mar. 13, 2014, now Pat. No. 8,893,948, which is a continuation of application No. 13/275,375, filed on Oct. 18, 2011, now Pat. No. 8,708,212.

(51) Int. Cl.
  *A61B 17/115* (2006.01)
  *A61B 17/072* (2006.01)
  *A61B 17/068* (2006.01)
  *A61B 17/29* (2006.01)

(52) U.S. Cl.
  CPC ........... *A61B 17/1155* (2013.01); *A61B 17/068* (2013.01); *A61B 17/0686* (2013.01); *A61B 17/07207* (2013.01); *A61B 17/115* (2013.01); *A61B 2017/07257* (2013.01); *A61B 2017/2927* (2013.01)

(58) Field of Classification Search
  CPC ............. A61B 17/068; A61B 17/0686; A61B 17/072; A61B 17/07207; A61B 17/07292; A61B 17/115; A61B 17/1155
  USPC ............... 227/19, 175.1, 175.2, 176.1, 178.1, 227/180.1; 606/139, 151, 153, 219
  See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |

(Continued)

FOREIGN PATENT DOCUMENTS

| | | |
|---|---|---|
| CA | 908529 A | 8/1972 |
| CA | 1136020 A1 | 11/1982 |

(Continued)

OTHER PUBLICATIONS

European Search Report for EP 12186173.6, date of completion is Feb. 1, 2013; 4 pages.

*Primary Examiner* — Scott A. Smith

(57) ABSTRACT

A tilt anvil assembly is disclosed which includes a center rod, a head assembly, and a torsion spring configured to pivot the head assembly relative to the center rod. The head assembly has a locking collar defining a locked position preventing pivotal movement of the head assembly, and an unlocked position allowing pivotal movement of the head assembly. The torsion spring selectively engages the locking collar to maintain the locking collar at either the locked or unlocked position.

13 Claims, 9 Drawing Sheets

(56) References Cited

U.S. PATENT DOCUMENTS

| | | |
|---|---|---|
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |

(56) References Cited

U.S. PATENT DOCUMENTS

| | | |
|---|---|---|
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |

(56) References Cited

U.S. PATENT DOCUMENTS

| | | | |
|---|---|---|---|
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,540,132 B2 | 9/2013 | Marczyk et al. |
| 8,708,212 B2 * | 4/2014 | Williams ............... 227/175.1 |
| 8,893,948 B2 | 11/2014 | Williams |
| 2003/0111507 A1 | 6/2003 | Nunez |
| 2005/0051597 A1 | 3/2005 | Toledano |
| 2005/0107813 A1 | 5/2005 | Gilete Garcia |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0144897 A1 | 7/2006 | Jankowski et al. |
| 2006/0201989 A1 | 9/2006 | Ojeda |
| 2006/0241692 A1 | 10/2006 | McGuckin et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0257082 A1 | 11/2007 | Milliman |
| 2008/0230581 A1 | 9/2008 | Marczyk et al. |
| 2009/0230170 A1 | 9/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 | 2/2010 | Milliman et al. |
| 2010/0051668 A1 | 3/2010 | Milliman et al. |
| 2010/0065607 A1 | 3/2010 | Orban, III et al. |
| 2010/0084453 A1 | 4/2010 | Hu |
| 2010/0089971 A1 | 4/2010 | Milliman et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0133319 A1 | 6/2010 | Milliman et al. |
| 2010/0147923 A1 | 6/2010 | D'Agostino et al. |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1 | 12/2010 | Milliman et al. |
| 2011/0006100 A1 | 1/2011 | Milliam |
| 2011/0006102 A1 | 1/2011 | Kostrzewski |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| WO | 8706448 A1 | 11/1987 |
| WO | 8900406 A1 | 1/1989 |
| WO | 9006085 A1 | 6/1990 |

* cited by examiner

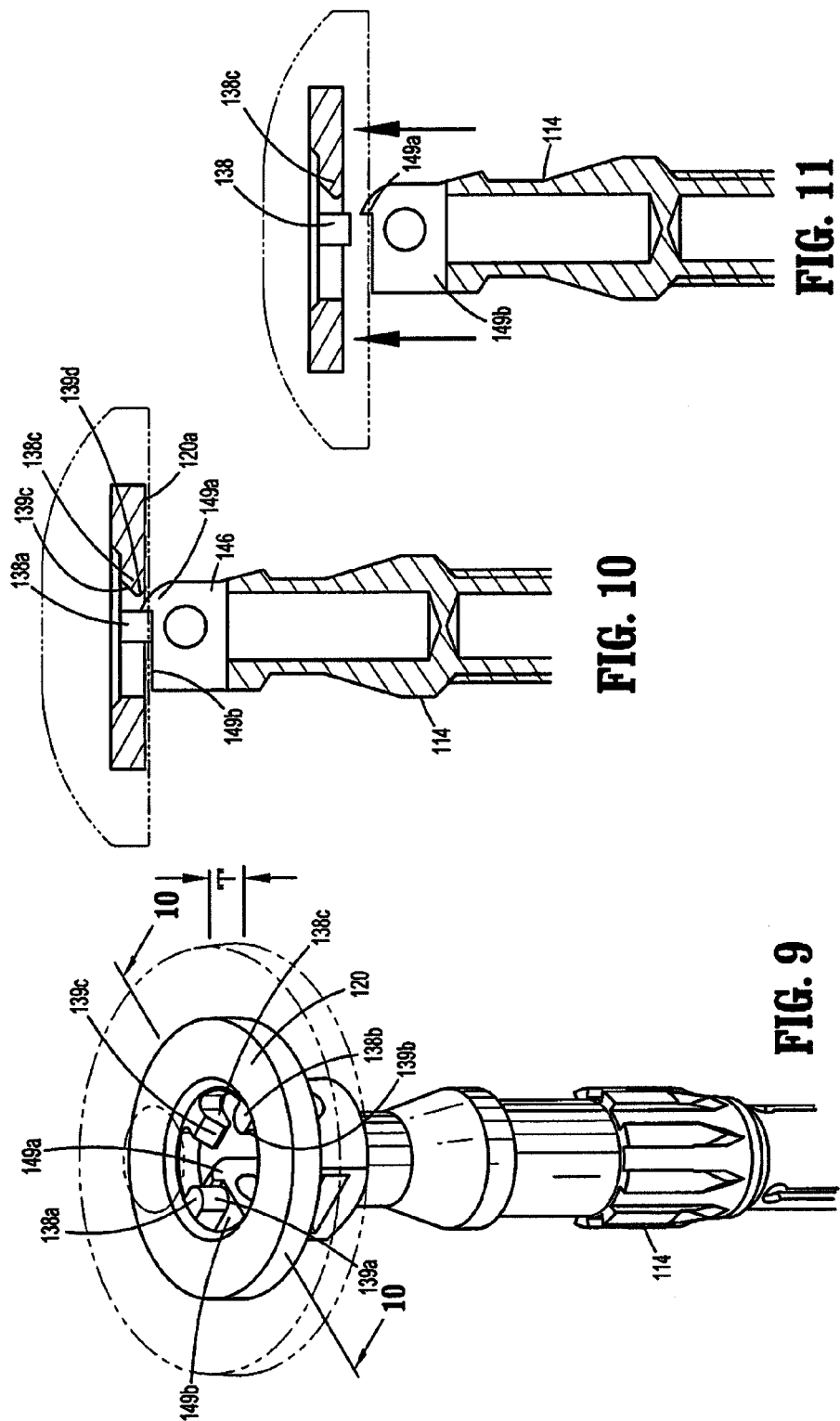

TILT TOP ANVIL WITH TORSION SPRING

CROSS-REFERENCE TO RELATED APPLICATIONS

This application is a continuation of U.S. patent application Ser. No. 14/207,729 filed Mar. 13, 2014, now U.S. Pat. No. 8,893,948, which is a continuation of U.S. patent application Ser. No. 13/275,375 filed Oct. 18, 2011, now U.S. Pat. No. 8,708,212, the disclosures of each of the above-identified applications are hereby incorporated by reference in their entirety.

BACKGROUND

1. Technical Field

The present disclosure relates generally to an anvil assembly which is suitable for use with a circular anastomosis stapler. More specifically, the present disclosure relates to an anvil assembly having a tiltable head which is suitable for use with a circular anastomosis stapler.

2. Description of Related Art

Circular anastomosis staplers which include an anvil assembly having a tiltable anvil head are known in the art. Such tiltable anvil heads have been disclosed in U.S. Pat. No. 7,431,191 ("the '191 patent") and U.S. Publication No. 2008/0230581 to Marczyk ("the '581 Publication"), the contents of which are incorporated herein by reference in their entirety. In some known circular anastomosis staplers, a locking collar or a backup plate located within the anvil assembly is positioned to inhibit tilting of the anvil head of the anvil assembly prior to firing of the stapler. Upon firing of the stapler, a knife blade of the stapler engages or becomes embedded into the locking collar, and moves the locking collar to a position which allows the anvil head to tilt upon retraction of the knife blade from the locking collar. If the locking collar sticks to the knife blade upon retraction of the knife blade, the locking collar may return to its position preventing tilting of the anvil head. Thus, the anvil head will not tilt.

In order to effect tilting of the anvil head upon retraction of the knife blade, both the '191 patent and the '581 Publication disclose a plunger and a plunger spring which engage a post on the anvil head to tilt the anvil head. To inhibit the locking collar from sticking to the knife blade and, the '191 patent and the '581 Publication disclose a retainer clip and a pivotal latch assembly, respectively, to engage the locking collar upon retraction of the knife blade.

Despite recent improvements to circular anastomosis instruments, a need still exists for an anvil head assembly with a simplified mechanism to effect tilting of the anvil head and to inhibit the locking collar from sticking to the knife blade upon retraction of the knife blade.

SUMMARY

The present disclosure features a tilt anvil assembly including a torsion spring for pivoting an anvil between a non-tilted position and a fully tilted position.

One aspect of the present disclosure features a tilt anvil assembly which includes a center rod, a head assembly, and a torsion spring. The head assembly includes a housing, a locking collar, and an anvil plate having staple deforming pockets. The torsion spring is configured to pivot the head assembly relative to the center rod.

The locking collar has a locked position preventing pivotal movement of the head assembly, and an unlocked position allowing pivotal movement of the head assembly.

In one embodiment, the torsion spring includes a coiled structure and at least one biasing member extending radially outwardly from the coiled structure. The at least one biasing member includes a middle member having an arcuate profile.

In some embodiments, the middle member is configured to engage the locking collar to facilitate holding the locking collar at a locked position inhibiting pivotal movement of the head assembly. The middle member may also be configured to engage the locking collar to maintain the locking collar at an unlocked position inhibiting proximal movement of the locking collar and allowing pivotal movement of the head assembly.

Another aspect of the present disclosure features a method for pivoting an anvil head assembly of a surgical anvil assembly. The method includes a step of providing an anvil assembly which includes a rod, a head assembly, a locking collar, and a torsion spring. The torsion spring is configured to pivot the head assembly relative to the rod. The torsion spring defines a normal configuration and a biased configuration. The method further includes a step of tilting the head assembly as the torsion spring transitions from the biased configuration to the original configuration.

The method may include the steps of locking the head assembly at a non-tilted position via the locking collar, and unlocking the head assembly from the non-tilted position.

The method may also include the steps of firing the stapler to advance a knife blade into the locking collar, moving the locking collar from a locked position inhibiting pivotal movement of the head assembly to an unlocked position allowing pivotal movement of the head assembly.

Further, the method may include the step of maintaining the locking collar at the unlocked position while extracting the knife blade from the locking collar.

DESCRIPTION OF THE DRAWINGS

Various embodiments of the presently disclosed tilt anvil assembly are disclosed herein with reference to the drawings wherein:

FIG. 9 is a cut-away view of the tilt anvil assembly shown in FIG. 2 with the anvil head in a locked, non-tilted position;

FIG. 10 is a side cross-sectional view of the tilt anvil assembly taken along the line 10-10 of FIG. 9;

FIG. 11 is a side cross-sectional view of the tilt anvil assembly shown FIG. 9 with the anvil head in an unlocked, non-tilted position;

DETAILED DESCRIPTION OF EMBODIMENTS

Figure 1:
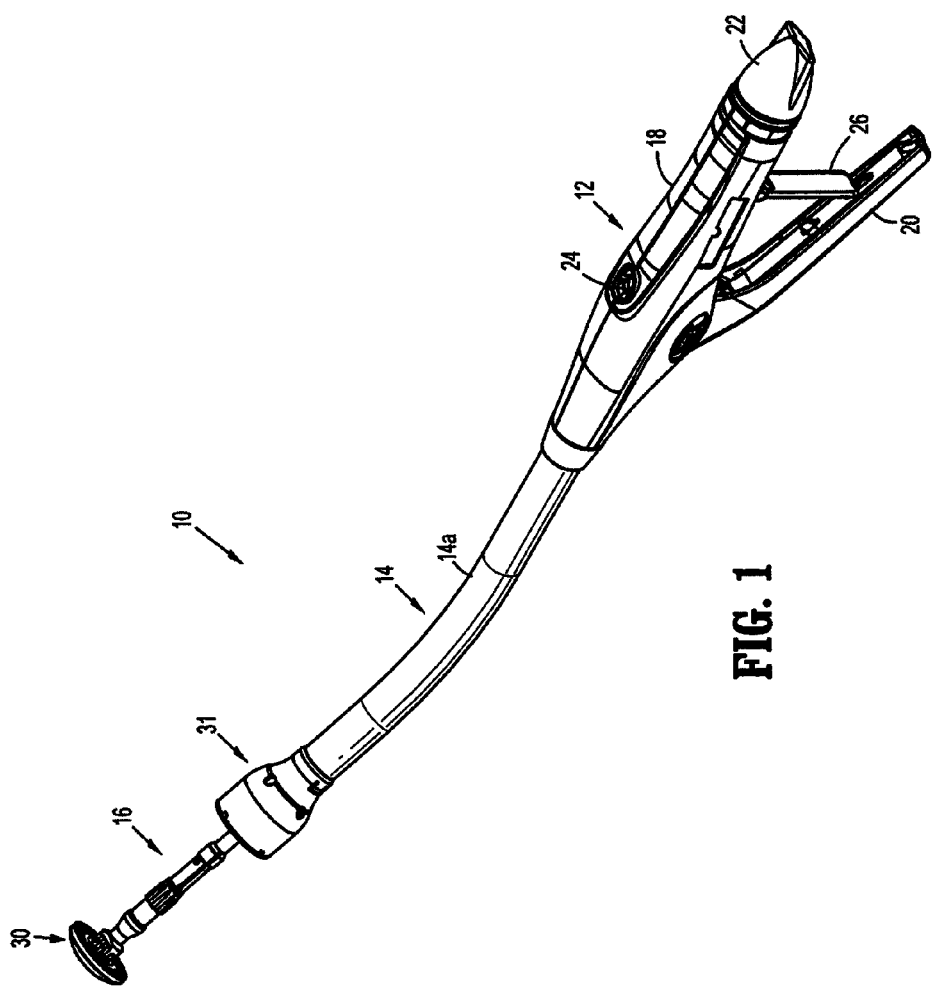
FIG. 1 is a perspective view of a surgical stapling device including an embodiment of an anvil assembly according to the present disclosure.

Embodiments of the presently disclosed anvil assembly will now be described in detail with reference to the drawings in which like reference numerals designate identical or corresponding elements in each of the several views. Throughout this description, the term "proximal" will refer to the portion of the instrument closest to the operator and the term "distal" will refer to the portion of the instrument furthest from the operator.

FIG. 1 illustrates an embodiment of a surgical stapling device configured for use with a tilt anvil assembly according to the present disclosure. Briefly, surgical stapling device 10 includes a proximal handle assembly 12, an elongated central body portion 14 including a curved elongated outer tube 14a, and a distal head portion 16. Alternately, in some surgical procedures, e.g., the treatment of hemorrhoids, it is desirable to have a substantially straight, shortened, central body portion. The length, shape and/or the diameter of body portion 14 and distal head portion 16 may also be varied to suit a particular surgical procedure.

With reference still to FIG. 1, handle assembly 12 includes a stationary handle 18, a firing trigger 20, a rotatable approximation knob 22 and an indicator 24. A pivotally mounted trigger lock 26 is fastened to handle assembly 12 and is manually positioned to inhibit inadvertent firing of stapling device 10. Indicator 24 is positioned on the stationary handle 18 and includes indicia, e.g., color coding, alpha-numeric labeling, etc., to identify to a surgeon whether the device is approximated and is ready to be fired. Head portion 16 includes an anvil assembly 30 and a shell assembly 31. For a more detailed discussion of surgical stapler 10, please refer to the '191 patent.

Figure 2:
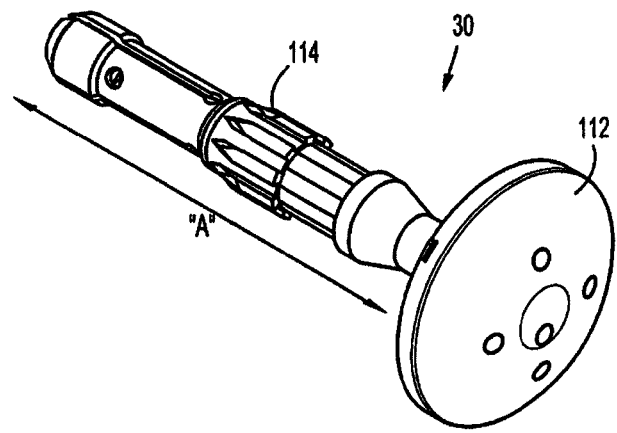
FIG. 2 is a front perspective view of the presently disclosed tilt anvil assembly with the anvil head untilted.
Figure 3:
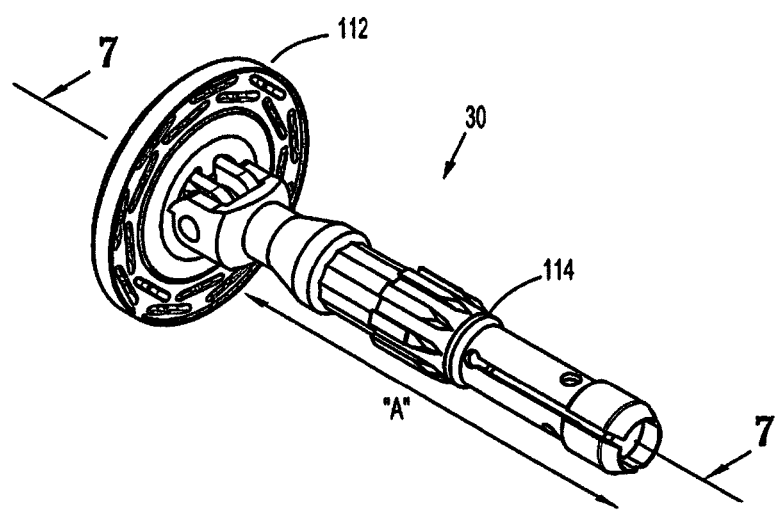
FIG. 3 is a rear perspective view of the tilt anvil assembly shown in FIG. 2.
Figure 12:
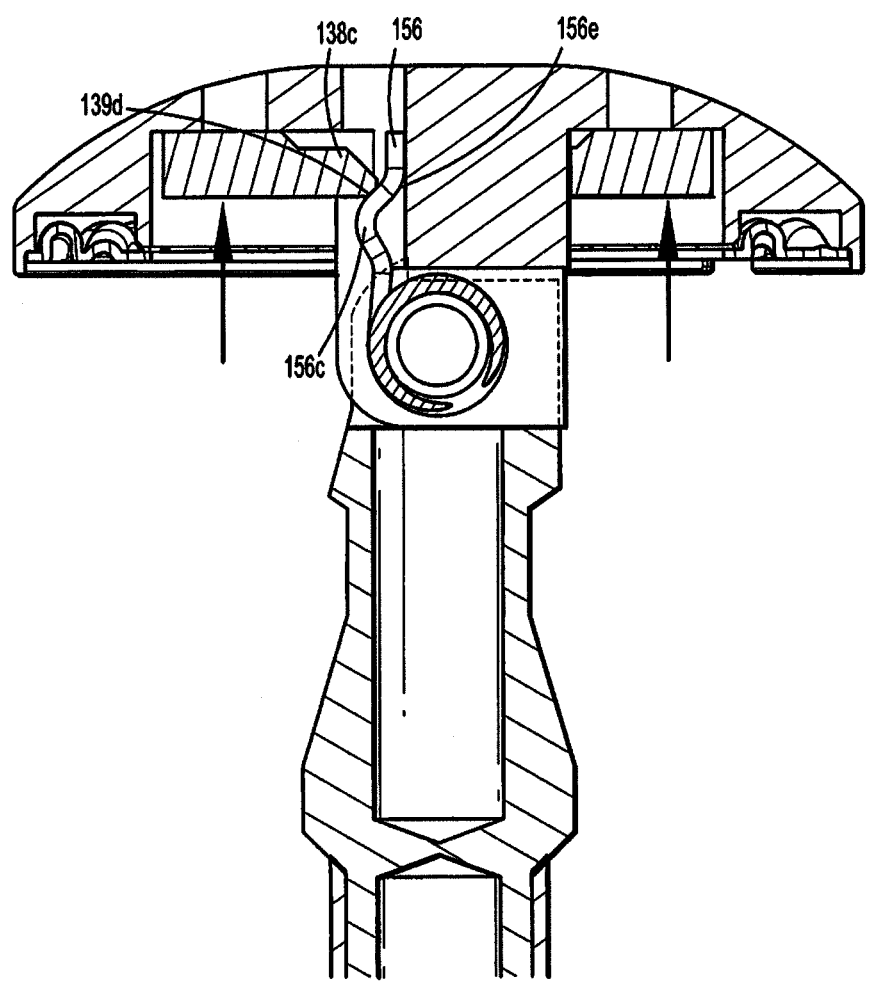
FIG. 12 is a side cross-sectional view of the tilt anvil assembly shown in FIG. 7 with the anvil head in an unlocked, non-tilted position.
Figure 14:
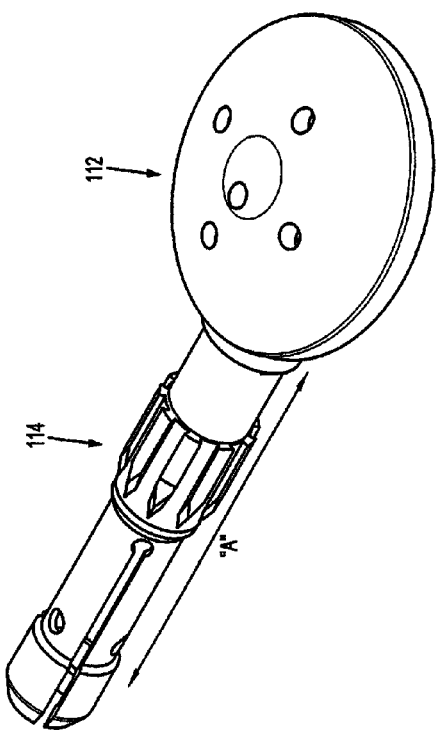
FIG. 14 is a side perspective view of the anvil assembly shown in FIG. 13.
Figure 13:
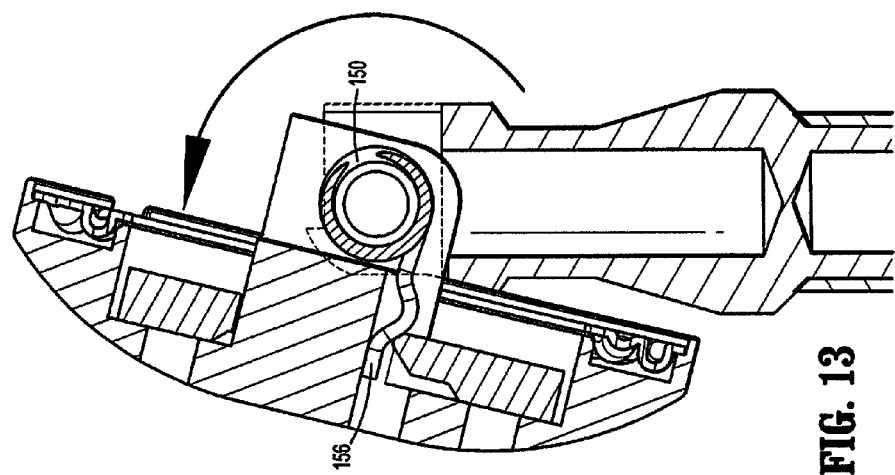
FIG. 13 is a side cross-sectional view of the tilt anvil assembly shown in FIG. 2 with the anvil head in a fully tilted position.

Referring now to FIGS. 2-17, an embodiment of the present disclosure is shown generally as anvil assembly 30. As illustrated in FIGS. 2-3, the anvil assembly 30 includes a head assembly 112 and a center rod assembly 114 which defines an axis "A" along its length. The anvil assembly 30 has a non-titled or operative position, at which the head assembly 112 is generally perpendicular to the center rod assembly 114. The anvil assembly 30 also has a fully tilted position, at which the head assembly 112 is substantially coaxially aligned with respect to the center rod assembly 114 (FIGS. 13 and 14). The head assembly 112 is pivotable with respect to the center rod assembly 114 between the non-tilted position and the fully tilted position.

Figure 4:
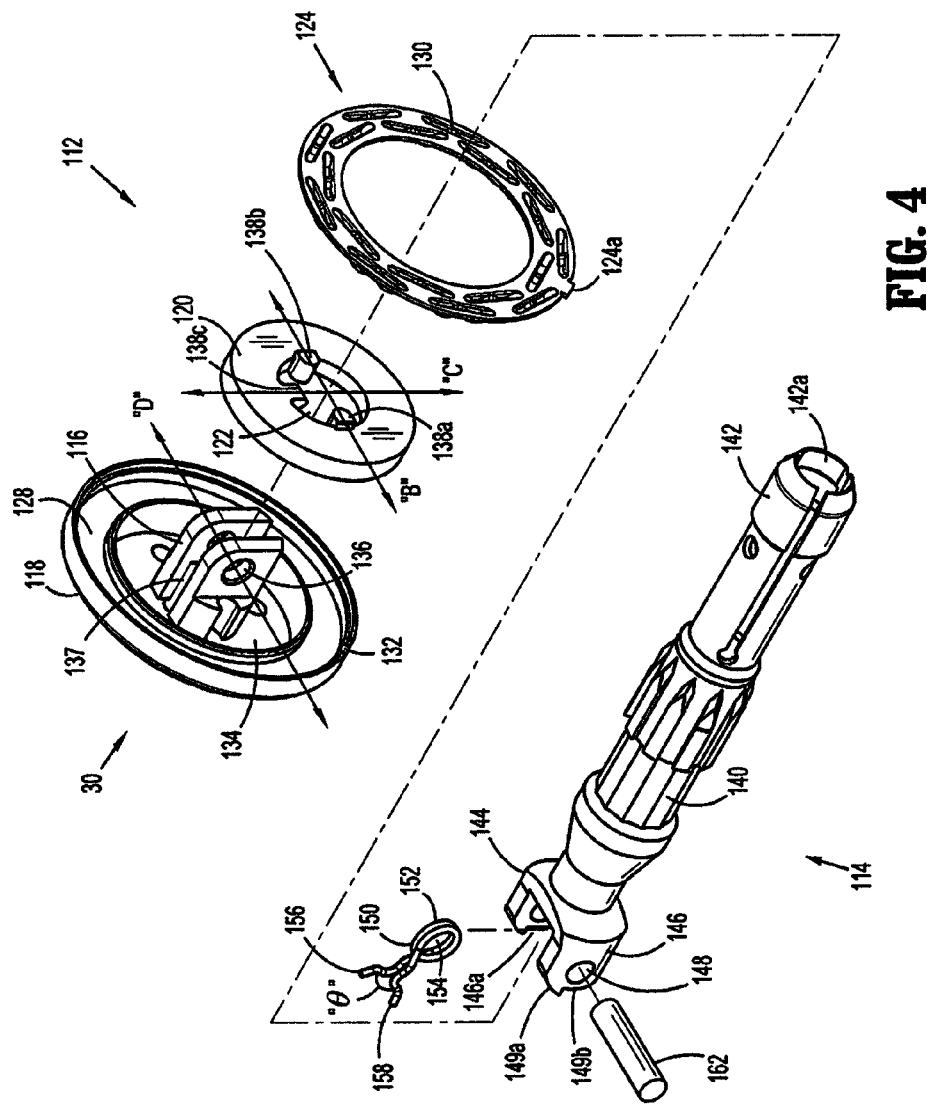
FIG. 4 is a rear perspective view, with parts separated, of the tilt anvil assembly shown in FIG. 2.

With reference to FIG. 4, the head assembly 112 includes a post 116, a housing 118, a locking collar 120, and an anvil plate 124. The post 116 is centrally positioned through a bore in the housing 118. Alternately, the post 116 may be integrally formed with the housing 118. The anvil plate 124 is supported on the housing 118 in an outer annular recess 128 and includes a plurality of pockets 130 for receiving and deforming staples. At least one tab 124a extends radially outwardly from the anvil plate 124 and is dimensioned to be received within a cutout 132 formed in the housing 118. The tab 124a and the cutout 132 function to align the anvil plate 124 within the annular recess 128.

The locking collar 120 includes a central opening 122 which is positioned about the post 116 within an inner recess 134 of the housing 118 between the post 116 and annular recess 128, such that the locking collar is slidably mounted about the post 116. The locking collar 120 may be formed from metal or other alternate materials.

In one embodiment, as illustrated in FIG. 4, the locking collar 120 includes three tabs 138a, 138b and 138c extending inwardly towards the central opening 122. The first and second tabs 138a, 138b are arranged in a manner such that they are diametrically opposed to each other along an axis "B", and the third tab 138c is placed equidistant from both the first and second tabs 138a, 138b on an axis "C" perpendicular to the axis "B." It is also envisioned that the locking collar 120 may include any number of tabs extending towards the central opening 122 arranged in any conceivable manner different from that described above.

In one embodiment, as seen in FIG. 9, each of the first and second tabs 138a-b has an internal surface 139a-b, respectively, and each internal surface 139a-b has a uniform arcuate, convex cross-sectional profile along the thickness "T" of the locking collar 120. However, as illustrated in FIGS. 9-10, the third tab 138c includes a first inclined internal wall 139c forming an acute angle with respect to a lower surface 120a of the locking collar 120. In some embodiments, the third tab 138c may also include a second inclined internal wall 139d between the first inclined internal wall 139c and the lower surface 120a and forming an obtuse angle with respect to the lower surface 120a. However, it is contemplated that the three tabs 138a-c may define other configurations different from that described above.

With reference to FIG. 4, the post 116 defines a pair of transverse throughbores 136 axially aligned with respect to a pivotal axis "D", which is parallel to the axis "B" of the locking collar 120. The post 116 also defines a transverse slot 137 perpendicular to the pivotal axis "B." The transverse slot 137 is dimensioned to accommodate the tab 138c of the locking collar 120 therein. When assembled, the locking collar 120 is slidably mounted about the post 116 with the third tab 138c slidably mounted within the transverse slot 137 of the post 136.

Figure 15:
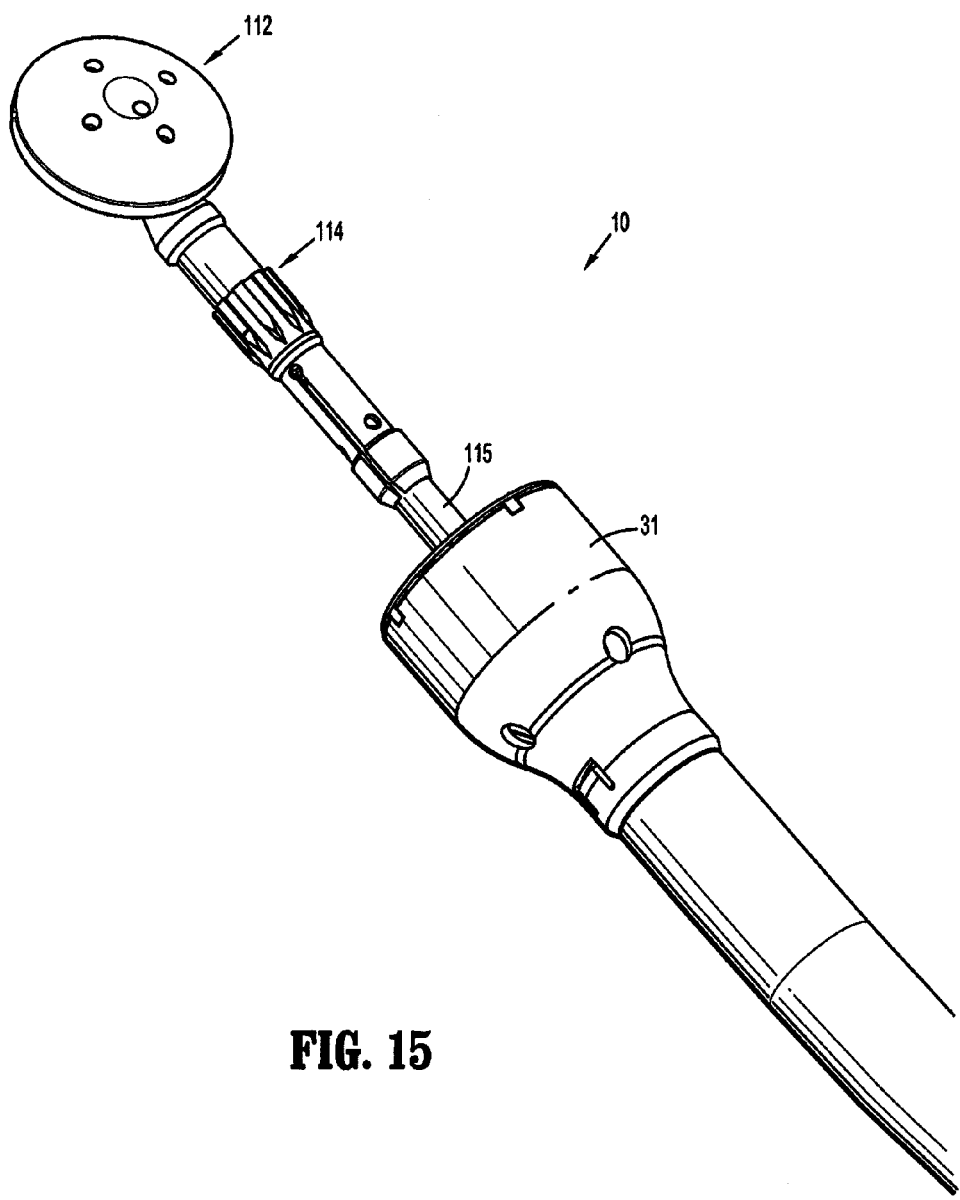
FIG. 15 is a perspective view of the surgical stapling device of FIG. 1 with the anvil head in a fully tilted position.

With continued reference to FIG. 4, the center rod assembly 114 includes a center rod 140 and a torsion spring 150 having a throughbore 154 defined therein. The center rod 140 includes a first end 142 defining a bore 142a therein dimensioned to releasably engage an anvil retainer 115 as shown in FIG. 15 to connect the anvil assembly 30 to the rest of the surgical stapling device 10. More detailed discussion of the anvil retainer 115 with which the anvil assembly 30 may be used is disclosed in the '191 patent. The center rod assembly 114 also includes a second end 144 having a pair of arms 146 which define a cavity 146a therebetween dimensioned to accommodate the torsion spring 150 and the post 116 therein. Each arm 146 defines a throughbore 148 therein.

When assembled, the post 116 and the torsion spring 150 are positioned within the cavity 146a of the center rod assembly 114, such that the throughbores 136 of the post 116, the throughbore 154 of the torsion spring 150 as well as the throughbores 148 of the center rod 140 are coaxially aligned along the pivotal axis "D," with a pivot member 162 disposed through the throughbores 148, 154 and 136. As a result, the torsion spring 150 engages both the head assembly 112 and the center rod assembly 114, causing the head assembly 112 to be pivotally secured to the center rod assembly 114 about the pivotal axis "D."

Figure 5:
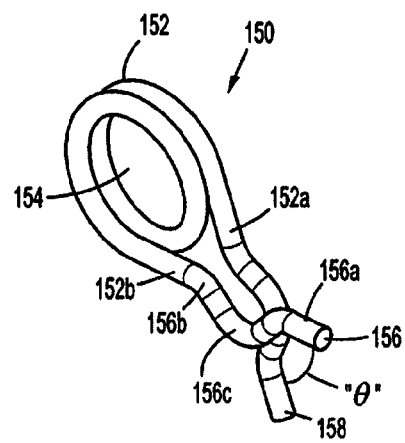
FIG. 5 is a perspective view of a torsion spring of the tilt anvil assembly shown in FIG. 4 in its original configuration.
Figure 6:
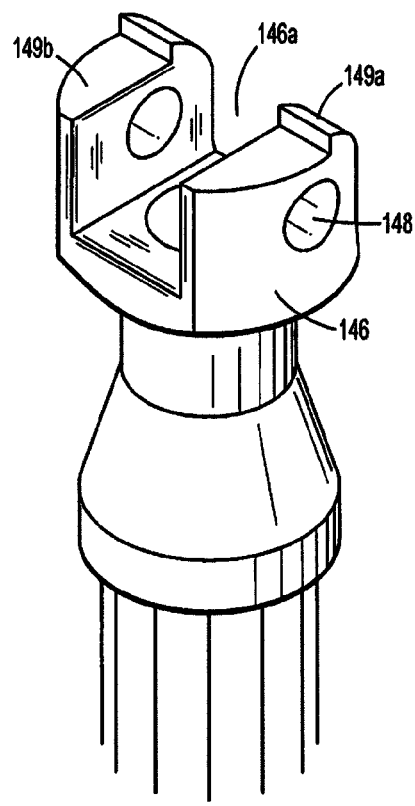
FIG. 6 is a perspective, distal view of a center rod assembly of the tilt anvil assembly of FIG. 4.
Figure 7:
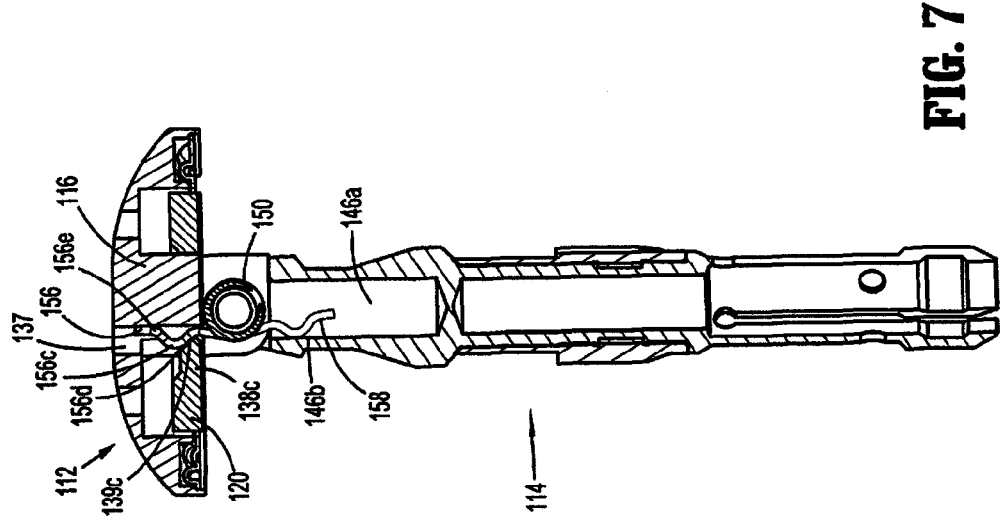
FIG. 7 is a cross-sectional view of the tilt anvil assembly taken along the line 7-7 of FIG. 3 with the anvil head in a locked, non-tilted position.

FIG. 5 illustrates one embodiment of the torsion spring 150. As illustrated in FIG. 5, the torsion spring 150 includes a coiled structure 152 which defines the throughbore 154 therein. The coiled structure 152 has a first end 152a and a second end 152b. The torsion spring 150 also includes two biasing members 156, 158 each extending radially outwardly from one end of the coiled structure 152. It is envisioned that in their normal, unbiased configuration, the two biasing members 156, 158 appear to intersect each other seen from the side as illustrated in FIGS. 4-5 and define an acute arcuate angle "θ" therebetween. The torsion spring 150 may comprise a deformable, elastic and resilient material. The two biasing members 156, 158 may be biased under an application of external force such that the two biasing members 156, 158 may extend in diametrically opposite directions as illustrated in FIG. 7. When biased as such, the torsion spring 150 exerts spring force to urge the two biasing members 156, 158 back to their normal, unbiased configuration as in FIGS. 4-5.

It is envisioned when the two biasing members 156, 158 are biased to extend diametrically opposite from each other, the head assembly 112 is in a non-tilted, operative position, whereas when the two biasing members 156, 158 are in their normal configuration, the head assembly 112 is in a fully tilted position. For instance, when the head assembly 112 is in a non-tilted, operative position as illustrated in FIG. 7, the two biasing members 156, 158 extend in diametrically opposite directions, and the torsion spring 150 exerts spring force to resume the two biasing members 156, 158 to their normal, configuration as illustrated in FIG. 5, which, in turn, urges the head assembly 112 to pivot about the rod assembly 114 about the pivotal axis "D". When the torsion spring 150 returns to their normal, unbiased configuration, the head assembly 112 is in a fully tilted position relative to the center rod assembly 114 as illustrated in FIGS. 13-14. Accordingly, the angle between the two biasing members in their normal configuration control the amount of rotation, or the extent of tilting of the head assembly 112 relative to the center rod assembly 114 from the non-tilted position to the fully tilted position.

The torsion spring 150 may exhibit other configurations. In some embodiments, the two biasing members 156, 158 in their normal configuration may define angles of any degree therebetween. In other embodiments, the torsion spring 150 may include only one biasing member 156 extending radially outwardly from the coiled structure 152.

Figure 8:
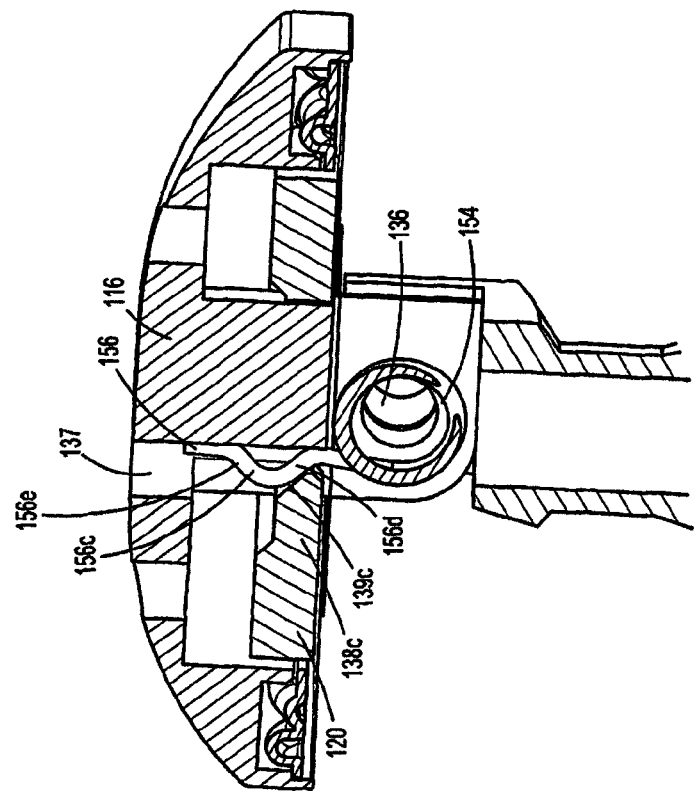
FIG. 8 is an enlarged view of the distal end of the tilt anvil assembly of FIG. 7.

With reference to FIGS. 7-8, the torsion spring 150 may be arranged in the anvil assembly 30 in a manner such that the first biasing member 156 of the torsion spring 150 extends distally into the housing assembly 112, specifically, in a space defined between the transverse slot 137 of the post 116 and the third tab 138c of the locking collar 120, and the second biasing member 158 extends proximally into the cavity 146a of the center rod assembly 114. It is envisioned that the second biasing member 158 may be securely fixed to an internal surface 146b of the cavity 146a by welding, gluing or other fastening mechanisms.

It is envisioned that the locking collar 120 may have two positions relative to the center rod assembly 114. In a first, locked position as illustrated in FIGS. 9-10, the center rod assembly 114 engages the locking collar 120 thereby preventing the head assembly 112 from pivoting about the center rod assembly 114. Specifically, each arm 146 the center rod 140 includes a protrusion 149a extending from a distal surface 149b thereof, configured to selectively engage one of the first and second tabs 138a-b of the locking collar 120. As seen in FIGS. 9-10, when the locking collar is in the first, locked position, each pair of the protrusions 149a and the distal surfaces 149b immediately abuts one the first and second tabs 138a-b of the locking collar 120. It is envisioned that the locking force exerted by the center rod assembly 114 on the locking collar 120 surpasses the spring force exerted by the torsion spring 150, thereby inhibiting the head assembly 112 from pivoting relative to the center rod assembly 114.

In a second, unlocked position as illustrated in FIG. 11, the protrusions 149a and distal surfaces 149b of the center rod assembly 114 disengage from the first and second tabs 138a-b of locking collar 120, thereby removing the locking force exerted on the locking collar 120, thus allowing the head assembly 112 to pivot about the center rod assembly 114 under the influence of the torsion spring 150.

It is envisioned that firing of the stapling device 10, or advancing surgical staplers into tissue, may transition the locking collar 120 from its locking position to its unlocked position. For instance, as illustrated in FIGS. 9-10, before firing the stapling device 10, the center rod assembly 114 secures the head assembly 112 to a pre-fired non-tilted position and limits pivotal movement of the head assembly 112.

Upon firing of the stapling device 10, the knife blade (not shown) engages with and becomes embedded into the locking collar 120. The knife blade moves the locking collar 120 into annular recess 128 of the housing 118 of the head assembly 112. When such movement occurs, as illustrated in FIG. 11, the first and second tabs 138a-b of the locking collar 120 move distally away and unlocks from protrusions 149a and distal surfaces 149b of the center rod 140, thereby unlocking the head assembly 112 from its non-tilted position.

In one embodiment, the torsion spring 150 may also be configured to facilitate holding the locking collar 120 in the locked and unlocked positions. For instance, as illustrated in FIG. 5, at least one of the biasing members of the torsion spring 150, e.g., the first biasing member 156 that extends into the housing assembly 112, may include two side portions 156a-b each generally exhibiting a straight, elongated configuration and a middle portion 156c exhibiting an arcuate configuration.

The middle portion 156c is configured to selectively engage the locking collar 120 to facilitate holding the locking collar 120 at either the locked or unlocked position. For instance, as illustrated in FIGS. 7-8, when the locking collar 120 is in the locked position, the third tab 138c formed on the locking collar 120 is disposed immediately proximally with respect to the middle portion 156c of the torsion spring 150. The first inclined internal wall 139c of the third tab 138c engages the proximal surface 156d of the middle portion 156c. As a result, the protrusion formed by the middle portion 156c prevents the locking collar 120 from moving distally to its unlocked position. Accordingly, the torsion spring 150 facilitates the center rod assembly 114 in holding the locking collar 120 at its locked position, thereby inhibiting unintended activation of the stapling device 10.

As discussed above, upon firing of the stapling device 10, the knife blade (not shown) engages or become embedded into the locking collar 120 and moves the locking collar 120 distally, unlocking the locking collar 120 from the center rod assembly 114, which, in turn, causes the locking collar 120 to move distally away from the center rod assembly 114. As illustrated in FIG. 12, during this process, the third tab 138c of the locking collar 120 moves distally away from and passes over the middle member 156c of the biasing member 156. As a result, the third tab 138c is situated distally with respect to the middle member 156c, and the second inclined internal wall 139d of the third tab 138c engages a distal surface 156e of the middle portion 156c. The protrusion formed by the middle portion 156c now inhibits the locking collar 120 from moving proximally. As a result, upon extraction of the knife blade from the locking collar 120, the middle portion 156c inhibits proximal movement of the locking collar 120, thereby maintaining the head assembly 112 in the unlocked position.

When the head assembly 112 is unlocked from its non-tilted position, as illustrated in FIG. 13-15, the torsion spring 150 exerts spring force to return the two biasing members 156, 158 to their normal configuration as illustrated in FIG. 5. As illustrated in FIG. 13, while the biasing member 156 rotates in a counterclockwise direction to resume the normal configuration, the biasing member 156 engages the post 116 and urges the head assembly 112 to tilt about the axis "D." It is envisioned that when the two biasing members 156, 158 of the torsion spring 150 resume their normal configuration, the head assembly 112 is fully tilted such that the head assembly 122 is substantially in line with the axis "A" of the center rod assembly 114 as illustrated in FIGS. 14-15.

It is noted that the head assembly 112 will not immediately tilt upon firing of the stapling device 10 because, upon firing, the head assembly 112 is in an approximated position, i.e., the anvil head assembly 112 is in close alignment with the shell assembly 31 of the stapling device 10. As such, the head assembly 112 will only begin to tilt when the head assembly 112 and the shell assembly 31 of the stapling device 10 are being unapproximated as illustrated in FIG. 15.

It will be understood that various modifications may be made to the embodiments disclosed herein. The above description should not be construed as limiting, but merely as exemplifications of preferred embodiments. Those skilled in the art will envision other modifications within the scope and spirit of the claims appended hereto.

What is claimed is:

1. A surgical instrument, comprising:
an anvil assembly including a head, a rod, and a biasing element, the anvil assembly having a first condition in which the head is non-pivotable with respect to the rod, and the anvil assembly having a second condition in which the head is pivotable with respect to the rod, the head of the anvil assembly including a collar and an anvil plate, the collar being longitudinally translatable with respect to the anvil plate, the biasing element being disposed in mechanical cooperation with the collar, and wherein when the anvil assembly is in its first condition, the collar is longitudinally movable from a first position where at least a portion of the collar is disposed proximally of a portion of the biasing element to a second position where at least a portion of the collar is disposed distally of the portion of the biasing element;
an elongated portion defining a longitudinal axis and configured to mechanically engage the anvil assembly; and
a knife assembly longitudinally translatable with respect to the elongated portion;
wherein a predetermined amount of longitudinal translation of the knife assembly with respect to the elongated portion causes the anvil assembly to switch from its first condition to its second condition.

2. The surgical instrument according to claim 1, wherein when the anvil assembly is in its first condition, the collar is in a proximal position with respect to the anvil plate, and wherein when the anvil assembly is in its second condition, the collar is in a distal position with respect to the anvil plate.

3. The surgical instrument according to claim 2, wherein the head of the anvil assembly is prevented from pivoting when the collar is in the proximal position with respect to the anvil plate, and wherein the head of the anvil assembly is capable of pivoting when the collar is in the distal position with respect to the anvil plate.

4. The surgical instrument according to claim 1, wherein the collar includes three tabs extending inwardly towards a central opening of the collar, wherein two of the three tabs are diametrically opposed to each other, and wherein a third tab is equidistant from the other two tabs.

5. The surgical instrument according to claim 1, wherein the biasing element includes a coiled structure and at least one biasing member extending radially outwardly from the coiled structure.

6. The surgical instrument according to claim 5, wherein the at least one biasing member of the biasing element includes two biasing members, and wherein the two biasing members of the biasing element have a normal configuration in which the two biasing members define an acute angle therebetween.

7. The surgical instrument according to claim 6, wherein the biasing element comprises a resilient material such that the two biasing members have a tendency to return to their normal configuration when biased.

8. The surgical instrument according to claim 5, wherein the at least one biasing member includes an arcuate middle member.

9. The surgical instrument according to claim 8, wherein the arcuate middle member is configured to engage the collar to facilitate holding the collar at a locked position which maintains the anvil assembly in its first condition.

10. The surgical instrument according to claim 8, wherein the arcuate middle member is configured to engage the collar to maintain the collar at an unlocked position preventing proximal movement of the collar and allowing pivotal movement of the head of the anvil assembly.

11. The surgical instrument according to claim 1, wherein the collar includes a tab to selectively engage the biasing element.

12. The surgical instrument according to claim 11, wherein the tab includes a first inclined internal wall and a second inclined internal wall.

13. The surgical instrument according to claim 1, wherein a portion of the biasing element extends through an opening of the collar.

* * * * *